United States Patent
Fiandor et al.

(10) Patent No.: US 6,645,960 B1
(45) Date of Patent: Nov. 11, 2003

(54) ANTIFUNGAL SORDARICIN DERIVATIVES

(75) Inventors: Jose Maria Fiandor, Madrid (ES); Sophie Huss, Madrid (ES)

(73) Assignee: Glaxo Wellcome S.A., Madrid (ES)

( * ) Notice: Subject to any disclaimer, the term of this patent is extended or adjusted under 35 U.S.C. 154(b) by 0 days.

(21) Appl. No.: 10/129,698

(22) PCT Filed: Nov. 10, 2000

(86) PCT No.: PCT/EP00/11112
§ 371 (c)(1),
(2), (4) Date: Sep. 24, 2002

(87) PCT Pub. No.: WO01/34583
PCT Pub. Date: May 17, 2001

(30) Foreign Application Priority Data

Nov. 11, 1999 (EP) .............................................. 99500210

(51) Int. Cl.[7] ..................... A61K 31/5377; A61P 31/00; C07D 265/32; C07D 413/12
(52) U.S. Cl. ..................... 514/230.8; 544/148; 544/153; 544/154
(58) Field of Search ................................. 544/148, 153, 544/154; 514/230.8

(56) References Cited

U.S. PATENT DOCUMENTS 6,410,528 B1 * 6/2002 Bueno et al. ................ 544/154

FOREIGN PATENT DOCUMENTS

| WO | 96/14326 | 5/1996 |
| WO | 96/14327 | 5/1996 |
| WO | 99/09974 | 3/1999 |
| WO | 99/09975 | 3/1999 |

OTHER PUBLICATIONS

Bueno et al, *Chemical Abstracts*, vol. 131, No. 337,207, 1999.*

Gargaloo–Viola, "Sordarins as antifungal compounds," *Curr. Opin. Anti–Infect. Invest. Drugs*, 1999, vol. 1 (3), pp. 297–305.

* cited by examiner

*Primary Examiner*—Robert W. Ramsuer
(74) *Attorney, Agent, or Firm*—Kathryn L. Sieburth; Mary E. McCarthy; Charles M. Kinzig

(57) ABSTRACT

A compound of general formula (I) and physiologically acceptable salts wherein R represents phthalidyl, (2-oxo-5-methyl-1,3-diox-olen-4-yl)methyl or the group $CHR_4OCO(O)pR_5$ wherein $R_4$ is hydrogen or $C_{1-4}$ alcyl, p is zero or I, $R_5$ is $C_{1-6}$ alkly, $C_{5-8}$ cycloalyl (optionally substituted by $C_{1-3}$ alkyl or carboxyl), $C_{1-4}$ alkyl substituted by $C_{1-3}$ alkoxy or carboxy), $C_{1-4}$ alkyl substituted by one or more groups selected from amino, ($C_{1-4}$ alkylamino di($C_{1-4}$ alkyl)amino or carboxyl, phenyl (optionally substituted by carboxyl or aminoalkyl, $C_{1-4}$ alkylaminoalkyl or di($C_{1-4}$ alkyl) aminoalcyl, or $R_5$ is a 5–8 membered heterocyclic group containing 1 or 2 heteroatoms selected from oxygen or nitrogen, processes for their preparation, pharmaceutical compositions containing them and their use in medicine.

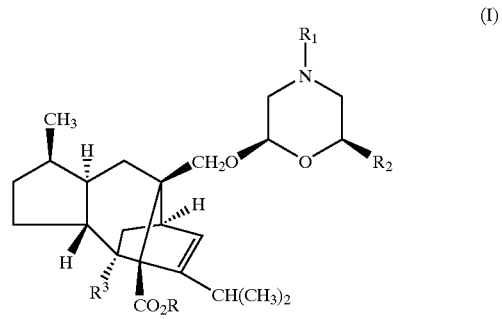

11 Claims, No Drawings

ANTIFUNGAL SORDARICIN DERIVATIVES

CROSS-REFERENCE TO RELATED APPLICATIONS

This application is filed pursuant to 35 U.S.C. §371 as a United States National Phase Application of International Application No. PCT/EP00/11112 filed Nov. 10, 2000, which claims priority from EP Application Serial No. 59500210.2 filed Nov. 11, 1999.

BACKGROUND OF THE INVENTION

This invention relates to novel carboxylic acid esters having antifungal activity. More particularly it relates to novel sordaricin derivatives, to processes for their preparation, to pharmaceutical compositions containing them and to their use in medicine, more particularly in the prevention or treatment of diseases in animals, including humans, caused by fungal infection.

British Patent Specification No. 1,162,027 describes the preparation of an antibiotic, SL2266, by the cultivation of the strain NRRL 3196 of the fungus species *Sordaria araneosa*. SL 2266, later named sordarin, is reported to have fungistatic activity. The same research group also described in Helvetica Chimica Acta (1971), 51, 119–120 the degradation of sordarin to sordaricin. Published Japanese Patent Application No. J6 2040292A describes the preparation of an antibiotic, zofimarin, which is reported to have antifungal activity.

Sordarin, sordaricin and zofimarin may be represented by formula (A) below

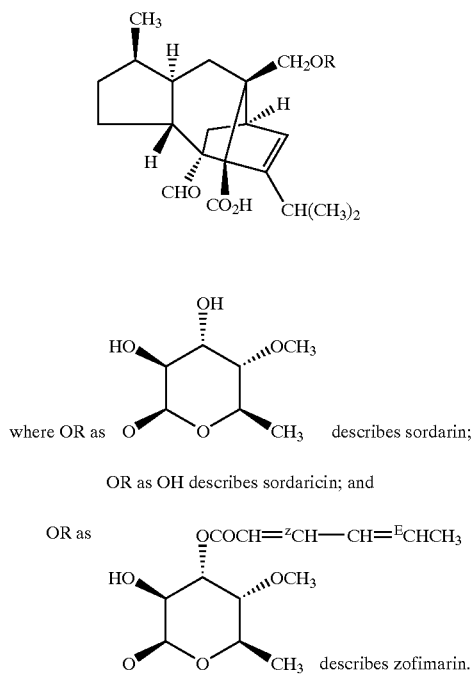

Although sordarin and zofimarin exhibit antifungal activity, both compounds are only moderately active and have limited spectra of action when tested against a battery of fungal organisms.

WO96/14326 and WO96/14327 describe novel sordarin derivatives which exhibit useful antifungal activity. WO99/09974 and WO99/09975 describe 4-cyano-4-deformyl sordarin and sordaricin derivatives which exhibit antingal activity.

DETAILED DESCRIPTION OF THE INVENTION

We have now found a novel group of sordaricin derivatives which exhibit a useful spectrum of antifungal activity when administered orally and which can be conveniently prepared from readily available starting material.

Thus according to a first aspect of the invention, we provide compounds of formula (I);

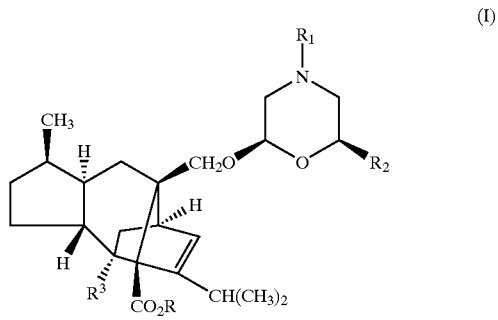

and physiologically acceptable salts wherein $R^1$ represents $C_{1-6}$ straight or branched chain alkyl, $C_{1-6}$ straight or branched chain alkoxy, optionally substituted phenoxy. $C_{3-6}$ straight or branched chain alkenyloxy (optionally substituted by 1 or 2 halogen atoms) or $C_{1-4}$ straight or branched alkoxy substituted by an optionally substituted phenyl group, $C_{3-8}$ straight or branched chain alkynyl, $C_{3-6}$ straight or branched chain alkenyl (optionally substituted by $C_{1-4}$ alkoxy or 1 or 2 halogen atoms), optionally substituted phenyl, optionally substituted $C_{3-7}$ cycloalkyl, optionally substituted $C_{5-7}$ cycloalkenyl, $C_{2-4}$ straight or branched chain alkyl substituted by ($C_{1-4}$ alkoxy, $C_{1-4}$ alkyl thio or halogen), $C_{1-4}$ straight or branched chain alkyl substituted by ($C_{1-4}$ alkoxycarbonyl, arylalkyloxycarbonyl, aryloxycarbonyl, propadienyl, cyano, optionally substituted $C_{3-7}$ cycloalkyl, optionally substituted 5 or 6 membered heteroaryl, or 1 or 2 optionally substituted phenyl groups), or methyl substituted by $C_{1-6}$ alkanoyl or optionally substituted benzoyl; $R_2$ represents a group selected from hydrogen, $C_{1-6}$ straight or branched chain alkyl, $C_{3-6}$ straight or branched chain alkenyl, optionally substituted phenyl or $C_{1-4}$ alkyl substituted with a group selected from $C_{1-4}$ alkoxy, hydroxy, acyloxy, alkoxycarbonyl or aryloxycarbonyl, and $R_3$ represents a group selected from formyl or cyano; R represents phthalidyl, (2-oxo-5methyl-1,3-dioxolen-4-yl)methyl or the group $CHR_4$ $OCO(O)pR_5$ wherein $R_4$ is hydrogen or $C_{1-4}$ alkyl, p is zero or 1, $R_5$ is $C_{1-6}$ alkyl, $C_{5-8}$ cycloalkyl (optionally substituted by $C_{1-3}$ alkyl or carboxyl), $C_{1-4}$ alkyl substituted by $C_{1-3}$ alkoxy or carboxyl, $C_{1-6}$ alkyl substituted by one or more groups selected from amino, ($C_{1-4}$ alkylamino di($C_{1-4}$ alkyl)amino or carboxyl, phenyl (optionally substituted by carboxyl or aminoalkyl, $C_{1-4}$ alkylaminoalkyl or di($C_{1-4}$ alkyl) aminoalkyl, or $R_5$ is a 5–8 membered heterocyclic group containing 1 or 2 heteroatoms selected from oxygen or nitrogen.

Physiologically acceptable salts of the compounds of formula (I) include salts formed with physiologically acceptable acids, and where the compound contains a carboxyl group then the invention also includes salts with a physiologically acceptable base.

Suitable physiologically acceptable acid addition salts includes those formed with inorganic acids such as hydrochloric acid, hydrobromic acid, phosphoric acid or sulphuric acid and organic acids such as acetic acid, propionic acid, succinic acid, lactic acid, tartaric acid, citric acid, maleic acid, benzoic acid or salicylic acid.

Suitable physioligically acceptable base addition salts include those formed with alkali and alkaline metal earths e.g. sodium or potassium salts, or with physiologically acceptable organic bases.

References hereinafter to a compound of formula (I) includes that compound and physiologically acceptable salts thereof.

Other salts which are not physiologically acceptable may be useful in the preparation of compounds of formula (I) and these form a further aspect of the invention.

It is to be understood that the present invention encompasses any individual isomers, including optical isomers and rotamers, of compounds represented by formula (I) above as well as mixtures thereof, including wholly or partially racemic mixtures thereof.

The term alkyl when used above to refer to a group or part of a group e.g. alkoxy includes straight or branched chain alkyl groups.

When $R_1$ is $C_{1-6}$ straight or branched chain alkyl group examples of such groups include methyl, ethyl, propyl, isopropyl, butyl, isobutyl, secondary butyl or tertiary butyl, pentyl, isopentyl, 1-ethylpropyl, hexyl or isohexyl.

When $R_1$ is $C_{1-4}$ straight or branched alkoxy substituted by optionally substituted phenyl examples of such groups include phenylmethoxy, phenylethoxy or phenylpropoxy.

When $R_1$ is $C_{1-6}$ straight or branched alkoxy examples of such groups include methoxy, ethoxy, propoxy, isopropoxy, butoxy, isobutoxy, pentoxy or hexyloxy.

When $R_1$ is a $C_{3-6}$ alkenyl group examples of such groups include allyl, 2-methylallyl, 3-methylallyl or 3,3-dimethylallyl.

When $R_1$ is a $C_{3-6}$ alkenyl group substituted by $C_{1-4}$ alkoxy this is conveniently $C_{3-6}$ alkenyl substituted by methoxy e.g. 2-methoxyallyl or 2-methoxymethylallyl.

When $R_1$ is $C_{3-6}$ alkenyl substituted by one or two halogen atoms this is conveniently $C_{3-6}$ alkenyl substituted by 1 or 2 halogen atoms selected from fluorine chlorine or bromine e.g. 2-fluoromethylallyl, 2-chloroallyl, 2-bromoallyl, 2-fluoroallyl, 3-fluoroallyl or 3,3-difluoroallyl.

When $R_1$ is $C_{3-6}$ alkenyloxy optionally substituted by 1 or 2 halogen atoms this is conveniently $C_{3-6}$ alkenyloxy optionally substituted by bromine or chlorine or fluorine e.g. allyloxy, 2-chloroallyloxy, 2-bromoallyloxy, 2-fluoroallyloxy.

The term aryl as a group or part of a group means optionally substituted phenyl.

The term optionally substituted phenyl as a group or part of a group e.g. phenoxy or phenylalkyl includes phenyl or phenyl substituted by 1 or 2 groups which may be the same or different and selected from $C_{1-4}$ alkyl, halogen (fluorine, chlorine, bromine or iodine), hydroxy, $C_{1-4}$ alkoxy, methylenedioxy or trifluoromethyl.

The term optionally substituted $C_{3-7}$ cydoalkyl as a group or part of a group is a cyclopropyl, cyclobutyl, cyclopentyl, cyclohexyl or cycloheptyl group which may be substituted by 1 or 2 methyl, methoxy, hydroxy or phenyl groups or may be fused to a phenyl ring to form a bicyclic ring system linked to the rest of the molecule via a carbon atom in with the cyloalkyl ring e.g. indanyl or tetrahydronaphthyl.

When $R_1$ is a $C_{2-4}$ alkyl group substituted by halogen examples of suitable groups include 2-chloroethyl, 2-fluoroethyl, trifluoroethyl.

The term straight or branched $C_{3-6}$ alkynyl includes 2-propynyl, 1-methyl-2-propynyl and 3-methyl-2-propynyl or 1,1-dimethyl-2-propynyl.

When $R_1$ is $C_{5-7}$ cycloalkenyl examples of such groups include cyclohexen-3-yl or cyclopenten-3-yl.

When $R_1$ is $C_{1-4}$ alkyl substituted by heteroaryl group, the term heteroaryl refers to a 5 or 6 membered heteroaryl group wherein the 5 membered group contains a single heteroatom selected from oxygen, sulphur or nitrogen and optionally contains 1 or 2 further nitrogen atoms, and the 6 membered group contains from 1 to 3 nitrogen atoms. Examples of such heteroaryl groups include furanyl, thienyl, pyrrolyl, oxazolyl, iso-oxazolyl, imidazolyl, pyrazolyl, thiazolyl, isothiazolyl, oxadiazolyl, thiadiazolyl, triazolyl, pyridyl, pyrimidiyl, pyridazinyl, pyrazinyl or triazinyl. The said heteroaryl groups may be substituted by one or two groups selected from $C_{1-4}$ alkyl e.g. methyl, hydroxyalkyl e.g. hydroxymethyl, acyloxyalkyl e.g. acetoxymethyl or halogen.

When $R_2$ is $C_{1-6}$ alkyl examples of such groups include methyl, ethyl, propyl, butyl, t-butyl.

When $R_4$ is $C_{1-4}$ alkyl examples of such groups include methyl, ethyl or propyl.

When $R_5$ is $C_{1-6}$ alkyl examples of such groups indude, methyl, ethyl or t-butyl.

When $R_5$ is $C_{5-8}$ cyloalkyl optionally subsitutued by $C_{1-3}$ alkyl or carboxy examples of such groups include cyclohexyl optionally substituted by $C_{1-2}$ alkyl e.g. 4-ethylcyclohexyl, or cyclohexyl subsitutued by carboxy at the 3 or 4 positions.

When $R_5$ is $C_{1-4}$ alkyl substituted by $C_{1-3}$ alkoxy examples of such a group include methoxymethyl or methoxyethyl. When $R_5$ is $C_{1-6}$ alkyl substituted by one or more amino, $C_{1-4}$ alkylamino, di($C_{1-4}$ alkyl)amino or carboxy groups examples of such groups include 2-amino-3-methylbutyl, 2-dimethylamino-3-methybutyl, 2-carboxyethyl, 3-carboxy-ethyl or 2-amino-3 carboxyethyl.

When $R_5$ is phenyl (optionally substituted carboxyl, aminoalkyl, $C_{1-4}$ alkylaminoalkyl or di($C_{1-4}$ alkyl) aminoalkyl examples of such groups include phenyl 4-carboxyphenyl, or 4-dimethylaminomethylphenyl.

When $R_5$ is a 5–8 membered heterocyclic group containing one or two heteroatoms selected from oxygen or nitrogen. Examples of such groups include piperidin-4-yl or tetrahydropyran-2-yl.

Examples of suitable $R_1$ groups include $C_{1-6}$ alkyl (such as methyl, ethyl, propyl, isopropyl, n-butyl, 1-methylpropyl, t-butyl, 1-ethylpropyl, pentyl, 3-methylbutyl, 3,3-dimethylbutyl), $C_{1-4}$ alkoxy e.g. methoxy, $C_{1-4}$ alkoxy substituted by phenyl (e.g. phenylmethoxy), phenoxy, $C_{2-4}$ alkyl substituted by $C_{1-4}$ alkoxy (e.g. methoxyethyl, ethoxyethyl, ethoxypropyl, isopropoxypropyl), $C_{2-4}$ alkyl substituted by $C_{1-2}$ alkylthio (e.g. ethylthioethyl), $C_{2-4}$ alkyl substituted by halogen (e.g. 2-chloroethyl, 2,2,2 trifluroethyl), $C_{1-4}$ alkyl substituted by cyano (e.g. cyanomethyl or cyanoethyl), $C_{1-4}$ alkyl substituted by propadienyl (e.g. 2,3-butadienyl) optionally substituted $C_{3-6}$ cycloalkyl e.g.[ (cyclopropyl optionally substituted by phenyl), cyclobutyl, cyclopentyl, cyclohexyl (optionally substituted by hydroxy or alkyl e.g. methyl), indanyl or tetrahydronaphthyl], phenyl, $C_{1-4}$ alkyl substituted by optionally substituted furanyl (e.g. furanylmethyl, hydroxymethylfuranylmethyl, acetoxymethylfuranylmethyl), pyridyl (e.g. pyridylmethyl or pyridylethyl), optionally substituted pyrrole e.g. (1-methylpyrrolemethyl) optionally substituted thiazolyl e.g. (thiazolylmethyl) optionally substituted imidazole e.g. N-hydroxymethylimidazolylmethyl, $C_{1-4}$ alkyl substituted by $C_{1-2}$ alkoxycarbonyl (e.g. methoxycarbonylethyl, 1-methoxycarbonyl-2-methylpropyl), aralkyloxycarbonyl (e.g. benzyloxycarbonylmethyl) or aryloxycarbonyl (e.g.

phenoxy carbonylmethyl), $C_{1-4}$ alkyl substituted by optionally substituted $C_{3-8}$ cycloalkyl (e.g. cyclopropylmethyl, cyclohexylmethyl, cyclohexylethyl, 1-yclohexylethyl), $C_{3-6}$ alkenyl (e.g. allyl, 2-methylallyl, 3-methylallyl, 3,3-dimethylallyl), $C_{3-8}$ alkenyl substituted by alkoxy e.g. 2-methoxyallyl, 2-methoxymethylallyl, $C_{3-6}$ alkenyl substituted by 1 or 2 halogen atoms selected from chlorine, bromine or fluorine e.g. (2-fluoromethylallyl, 2-chloroallyl, 2-bromoallyl, 2-fluoroallyl, 3-fluoroallyl, 3,3-difluoroallyl), $C_{3-6}$ alkenyloxy optionally substituted by halogen (e.g. allyloxy, 2-chloroallyloxy), $C_{1-4}$ alkyl substituted by 1 or 2 optionally substituted phenyl groups [wherein the optional substituent in the phenyl ring is selected from 1 or 2 halogen atoms, e.g. chlorine or fluorine, trifluromethyl, hydroxy, methoxy or methylenedioxy; (examples of such groups include optionally substituted benzyl e.g. benzyl, 4-methoxybenzyl, 4-trifluromethylbenzyl, difluorobenzyl such as 2,6-diflurobenzyl, 3,4-diflurobenzyl, 2,5-difluorobenzyl, or 2,4-difluorobenzyl, methylenedioxybenzyl, 1-phenyl ethyl, phenethyl (optionally substituted by 1 or 2 hydroxyl groups, methoxy, halogen e.g. fluorine or chlorine), phenylpropyl or diphenylmethyl)], $C_{3-8}$ alkynyl e.g. 2-propynyl, 1-methyl-2-propynyl, 3-methyl-2-propynyl, $C_{5-7}$ cycloalkenyl e.g. 1-cyclohexen-3-yl, or methyl substituted by acetyl or benzoyl.

Examples of suitable $R_2$ groups include methyl, ethyl, t-butyl and phenyl.

Conveniently R is a group selected from phthalidyl, (2-oxo-5-methyl-1,3-dioxolen-4-yl) methyl or the group $HC(R_4) OCO(O)pR_5$ wherein $R_4$ is hydrogen or methyl and $R_5$ is ethyl, t-butyl, 2-amino-3-methyl butyl, 2-carboxy-2-aminoethyl, 4-carboxyphenyl or 4-dimethylaminomethyl and more preferably p is zero.

Conveniently $R_1$ is a group selected from $C_{1-6}$ alkyl e.g. methyl, ethyl, propyl, isopropyl, butyl, 1-methylpropyl, t-butyl, n-pentyl, 3-methylbutyl, $C_{1-4}$ alkoxy e.g. methoxy, $C_{3-6}$ alkenyloxy (optionally substituted by halogen e.g. allyloxy, 2-chloroallyloxy), optionally substituted phenyl e.g. phenyl, $C_{3-6}$ cycloalkyl e.g cyclopropyl, cyclobutyl, cyclopentyl, indanyl, tetrahydronaphthyl, $C_{2-4}$ alkyl substituted by $C_{1-2}$ alkoxy, e.g. methoxyethyl or ethoxypropyl, $C_{2-4}$ alkyl substituted $C_{1-2}$ alkylthio e.g. ethylthioethyl, $C_{1-4}$ alkyl substituted by cyano e.g. cyanoethyl or cyanomethyl, $C_{1-4}$ alkyl substituted by propadienyl e.g. 2,3-butadienyl, $C_{1-4}$ alkyl substituted by alkoxycarbonyl (e.g. methoxycarbonylmethyl), $C_{1-4}$ alkyl substituted by $C_{3-7}$ cycloalkyl e.g. cyclopropylmethyl, $C_{1-4}$ alkyl substituted by heteroaryl e.g. furylmethyl, pyridylmethyl, N-methylpyrrolylmethyl or thiazolylmethyl, $C_{1-4}$ alkyl substituted by 1 or 2 optionally substituted phenyl groups e.g phenylmethyl, diphenylmethyl, difluorophenylmethyl (wherein the two fluorine atoms are in the 2,6, 2,4, 3,4 or 3,5 positions), trifluromethylphenylmethyl, methylenedioxyphenylmethyl, methoxyphenylmethyl, 1-phenylethyl or phenylethyl, $C_{3-6}$ alkenyl e.g allyl, 2-methylallyl, 3-methylallyl, 3,3-dimethylallyl, $C_{3-6}$ alkynyl e.g. 2-propynyl, $C_{3-6}$ alkenyl substituted by $C_{1-4}$ alkoxy e.g. 2-methoxyallyl, 2-methoxymethylallyl, $C_{3-6}$ alkenyl substituted 1 or 2 halogen atoms selected from chlorine, bromine or fluorine e.g. 2-chloroallyl, 2-bromoallyl, 2-fluoromethylallyl, 2-fluoroallyl, 3-fluoroallyl, 3,3-difluoroallyl, $C_{5-7}$ cycloalkenyl e.g cyclohexen-3-yl or methyl substituted by acetyl or benzoyl.

Preferred $R_1$ groups include, methyl, ethyl, propyl, isopropyl, butyl, 1-methylpropyl, 3-methylbutyl, methoxy, cyclopropyl, allyl, 2-methylallyl, allyl substituted by halogen e.g. 2-chloroallyl, 2-fluoromethylallyl, 2-bromoallyl, 3,3-difluoroallyl, phenyl, ethylthioethyl, methoxyethyl, benzyl, furylmethyl, 2,6-difluorophenylmethyl, 3,4-difluorophenylmethyl, 3,5-difluorophenylmethyl, 3,4-methylenedioxyphenylmethyl, 4-methoxyphenylmethyl, 1-phenylethyl or propynyl, 2,3-butadienyl, allyloxy, 2-chloroallyloxy.

Preferred $R_2$ groups include methyl, ethyl, t-butyl or phenyl and more particularly methyl.

A preferred $R_3$ group is CHO.

A preferred group of compounds of formula (I) are those wherein $R_2$ is methyl and more particularly where $R_3$ is also CHO.

Preferred R groups include phthalidyl or $CH(R_4)OCO(O)pR_5$ wherein $R_4$ is hydrogen or methyl and $R_5$, ethyl or t-butyl and p is zero or 1.

Compounds according to the inventions when administered orally exhibit a high level of antifungal activity against a wide range of pathogenic micro-organisms. Thus the compounds of formula (I) are useful in combating fungal and or protozoal infections in animals, including humans. For example, they may be used in the treatment of fungal infections including those caused by one or more organisms such as species of Candida (e.g. *Candida albicans, Candida glabrata, (Torulopsis glabrata), Candida tropicalis, Candida parapsilosis* and *Candida pseudotropicalis*), *Cryptococcus neoformans*, Aspergillus Spp (e.g. *Aspergillus flavus* and *Aspergillus fumigatus*), Coccidioides (e.g. *Coccidioides immitis*), Paracoccidioides (e.g. *Paracoccidioides brasiliensis*), Histoplasma (e.g. *Histoplasma capsulatum*) or Blastomyces (e.g. *Blastomyces dermatitidis*). They may also be used to treat other fungal infections caused by species of Trchophyton, Microsporum or Epidermophyton (e.g. *Trichophyton mentagrophytes, Trichophyton rubrum, Microsporum canis* or *Epidermophyton floccosum*), or in mucosal infections caused by *Candida albicans*.

Compounds of formula (I) may also be used to treat other infections caused by other fungi such as Geotrichum (e.g. *Geotrichum clavatum*), Trichosporon (e.g. *Trichosporon beigelii*), Blastoschizomyces (e.g. *Blastoschizomyces capitatus*), Sporothrix (e.g. *Sporothrix schenckii*), Scedosporium (e.g. *Scedosporium apiosperum*), Cladosporium (e.g. *Cladosporium carrionii*) and *Pityrosporum ovale*.

The compounds of formula (I) may also be used to treat infections caused by protozoa such as Toxoplasma, Cryptosporidium, Leishmania, Tripanosoma, Giardia and Trichomonas.

The compounds of formula (I) may also be used to treat infections caused by *Pneumocystis Carinii*.

The antifungal activity of the compounds of formula (I) may be determined using conventional in vitro and in vivo screens.

The in vitro evaluation of the anti-fungal activity of compounds of the invention was performed on liquid or solid medium by the anti-fungal two-fold serial dilution technique of determining the minimum inhibitory concentration (MIC) of anti-fungal agent that inhibited development of growth after 24 to 48 hours of incubation at 37° C. For example a series of agar plates or broth microdilution panels containing two-fold dilutions of anti-fungal agent were inoculated with a standard culture of a clinically relevant pathogen, in the presence and absence of activated or inactivated serum. The agar plates or broth microdilution panels were then examined for the presence or absence of growth of the fungus and the appropriate MIC values determined. The compounds of the invention show little or no activity when the test is carried out in the absence of activated or inactivated serum, but exhibit significant activity when the test is carried out in the presence of the serum.

The fungicidal activity of the compounds of formula (I) may also be determined in conventional in vivo tests in animals e.g. rats and mice, such as the lethal systems candidiasis test in mice.

Compounds of the invention show particularly useful activity against one or more of the organisms selected from *Candida albicans, Candida glabrata, Candida tropicalis, Candida parapsilosis, Pneumocystis carini Coccidioides immitis, Paracoccidioides brasiliensis, Histoplasma capsulatum* and *Blastomyces dermatitides*.

In view of their antifungal and or antiprotozoal activity, compounds of formula (I) recommend themselves for the treatment of a variety of fungal and or protozoal infections in human beings and animals. Such infections include superficial, cutaneous, subcutaneous and systemic mycotic infections such as respiratory tract infections, gastrointestinal tract infections, cardiovascular infections, urinary tract infections, CNS infections, candidiasis and chronic mucocandidiasis (e.g. thrush and vaginal candidiasis) and skin infections caused by fungi, cutaneous and mucocutaneous candidiasis, dermatophytoses including ringworm and tinea infections, athletes foot, paronychia, pityriasis versicolor, erythrasma, intertrigo, fungal nappy rash, candida vulvitis, candida balanitis and otitis extema. They may also be used as prophylactic agents to prevent systemic and topical fungal infections. Use as prophylactic agents may, for example, be appropriate as part of a selective gut decontamination regimen in the prevention of infection in immunocompromised patients (e.g. AIDS patients, patients receiving cancer therapy or transplant patients). Prevention of fungal overgrowth during antibiotic treatment may also be desirable in some disease syndromes or iatrogenic states. They may also be used in the prophylaxis and or treatmentof infections caused by *Pneumocystis carinii*.

Thus in a further aspect the invention provides a method of the treatment of human or non human animal body to prevent or treat fungal and or protozoal diseases, which method comprises administering to solid body an effective amount of a compound of formula (I).

The invention also provides for the use of a compound of formula (I) in the manufacture of a medicament for the treatment or prevention of fungal and or protozoal infections.

While it is possible that, for use in therapy, compounds of the invention may be administered as the raw chemical, it is preferable to present the active ingredient as a pharmaceutical formulation. The invention thus further provides a pharmaceutical formulation comprising compounds of formula (I) and physiologically acceptable salts thereof together with one or more pharmaceutically acceptable carriers thereof and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, implant, rectal, topical, ophthalmic or genito-urinary administration or in a form suitable for administration by inhalation or insulffation.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate or crosscarmellose sodium; wetting agents such as sodium lauryl sulphate and pH modifiers for example citric acid, malic acid, tartaric acid, sodium carbonate, sodium bicarbonate, triethanolamine or trometamol. The capsule may contain powders, tablets, pellets, granules, liquids, waxes, surfactants or any combination of the former, which may be coated according to the methods well known to the art. The content of the capsules can be made of: binding agents, fillers, lubricants, desintegrants, wetting agents and pH modifiers, as described above. The tablets which include chewable, dispersible or effervescent tablets may be coated according to methods well known in the art.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid and flavouring agent.

For buccal administration the composition may take the form of tablets or lozenges formulated in conventional manner.

For administration by inhalation the compositions according to the invention are conveniently delivered in the form of an aerosol spray presentation from pressurised packs with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation the compositions according to the invention may take the form of a dry powder composition, for example a powder mix of the compound and a suitable powder base such as lactose or starch or as a modified physical form of the drug substance alone. The powder composition may be presented in unit dosage form in, for example, capsules or cartridges of e.g. gelatin, or blister packs from which the powder may be administered with the aid of an inhaler or insulator.

The compositions may take the form of a suppository, e.g. containing a conventional suppository base, or a pessary, e.g. containing a conventional pessary base.

The compositions may also be formulated for topical administration in the form of ointments, creams, gels, lotions, shampoos, powders (including spray powders), pessaries, tampons, sprays, dips, aerosols, drops (e.g. eye, ear or nose drops) or pour-ons. Ointments and creams may, for example, be formulated with an aqueous or oily base with the addition of suitable thickening and/or gelling agents. Ointments for administration to the eye may be manufactured in a sterile manner using sterilised components. Pour-ons may, for example, be formulated for veterinary use in oils containing organic solvents, optionally with formulatory agents, e.g. stabilising and solubilising agents. Pessaries and tampons for vaginal insertion may be formulated using conventional techniques and, where appropriate, may contain an effervescent vehicle. Such compositions may also contain other active ingredients such as corticosteroids, antibiotics or antiparasitics as appropriate.

Liquid preparations for intranasal delivery may take the form of solutions or suspensions and may contain conventional excipients such as tonicity adjusting agents, for example, sodium chloride, dextrose or mannitol; preservatives, for example benzalkonium chloride, thiomersal, phenylethyl alcohol; and other formulating agents such as suspending, buffering, stabilising, dispersing and or flavouring agents.

Transdermal administration may be affected by the design of a suitable system which promotes absorption of the active compound through the skin and would typically consist of a base formulation enclosed within an adhesive stick-on patch comprising backing films, membranes and release liners. Such systems may include absorption enhancers such as alcohols or work by promoting ionotophoresis.

The composition according to the invention may also be formulated as a depot preparation. Such long acting formulations may be administered by implantation (for example subcutaneously or intramuscularly) or by intramuscular injection. Thus, for example, a compound of the invention may be formulated with suitable polymeric or hydrophobic materials (for example as an emulsion in an acceptable oil) or ion exchange resins, or as sparingly soluble derivatives, for example, as a sparingly soluble salt.

When the compositions comprise dosage units, each unit will preferably contain 0.001 mg to 1000 mg, advantageously 0.01 mg to 400 mg, of active ingredient where a compound of the invention is to be administered orally. The daily dosage as employed for adult human treatment will preferably range from 0.001 mg to 5000 mg of active ingredient, most preferably from 0.01 mg to 2000 mg which may be administered in 1 to 4 daily doses, for example, depending on the route of administration and on the condition of the patient and the disease to be treated.

The compound may be administered by intravenous infusion using, for example, up to 50 mg/kg/day of the active ingredient. The duration of treatment will be dictated by the rate of response rather than by arbitrary numbers of days.

Compounds of the invention may also be used in combination with other therapeutic agents, and the invention thus provides, in a further aspect, a combination comprising a compound of the invention together with another therapeutically active agent.

Thus for example the compounds of the invention may be used in combination with one or more other antifungal agents, such as a polyenic derivative e.g. (Amphotericin B, Nystatin, a lipid formulation of Amphotericin B) an azole derivative e.g. (Fluconazole, Intraconazole, Ketoconazole, Miconazole, Clotrimazole, ZD-08070, UK-109496), 5-Fluorocytosine, a Pneumocandin or Echinocandin derivative (such as Cilofungin, LY-303366, L-733560), an allylamine derivative (e.g. Terbinafine, Butenafine or Naftifine), and/or one or more immunomodulating agents such as an interferon e.g. (IFN-γ), interleukine e.g. (IL-1, IL-2, IL-3 and IL-8) and colony stimulating factors, [(G)-CSF, (M)-CSF and (GM)-CSF] and defensines. Particularly advantageous compounds for use with compounds of the invention include Intraconazole, Flucytosine, Fluconazole, Terbinafine or Amphotericin B.

When the compounds of the invention are administered in combination with another antifungal agent the compounds of the invention and the other fungal agent can be administered at the recommended maximum clinical dosage or at lower doses.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention. The individual components of such combinations may be administered either sequentially or simultaneously in separate or combined pharmaceutical formulations.

When a compound of the invention is used in combination with a second therapeutic agent against the same condition the dose of each compound may differ from that when the compound is used alone. Appropriate doses will be readily appreciated by those skilled in the art.

According to another aspect of the present invention, we provide a compound of formula (I) or a physiologically acceptable salt thereof or a pharmaceutical composition comprising a compound of formula (I) or a physiologically acceptable salt thereof as defined above for use in therapy, particularly for the treatment of fungal infections in animals (especially humans).

According to another aspect of the present invention, we provide the use of a compound of formula (I) or a physiologically acceptable salt thereof in the manufacture of a medicament for the treatment of fungal infections in a human or non-human animal patient.

According to a further aspect of the present invention, we provide a method of treatment of the human or non-human animal body to combat fungal diseases, which method comprises administering to said body an effective amount of a compound of formula (I) or a physiologically acceptable salt thereof.

It will be appreciated by those skilled in the art that references herein to treatment extend to prophylaxis as well as the treatment of established conditions or infections.

The invention also provides processes for the preparation of compounds of formula (I).

The compounds of formula (I) may be readily prepared by esterification of the corresponding carboxylic acid (II) or an alkali metal salt thereof wherein $R_1$, $R_2$ and $R_3$ have the meaning defined in formula (I).

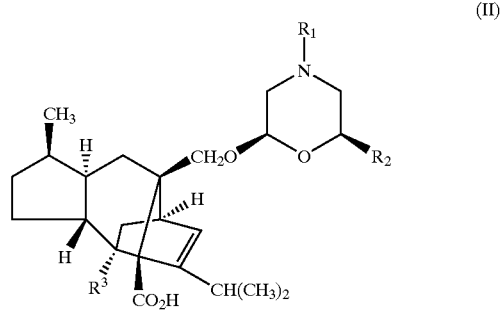

(II)

by reaction with the compound R Y wherein R has the meanings defined in formula (I) or is a group convertible thereto and Y is a leaving group e.g. a halide. Conveniently the reaction is carried out in a polar solvent such as an ester e.g. ethyl acetate and or di-methylformamide, dimethylacetamide or N-methyl pyrrolidinone in the presence of a base e.g. an inorganic base such as sodium carbonate or bicarbonate and in the presence of a quaternary ammonium salt such as a tetrabutyl ammonium halide e.g. bromide or iodide.

The compounds of formula (II) may be prepared by the processes described and/or exemplified in WO99/58512 and which is incorporated herein by reference.

Compounds of formula (I) wherein R is the group $CHR_4OCO(O)pR_5$ and $R_4$ is hydrogen may be prepared by reaction of the halomethyl ester (III), wherein $R_1$, $R_2$ have the meaning given on formula II and $R_3$ is formyl or a protected formyl group,

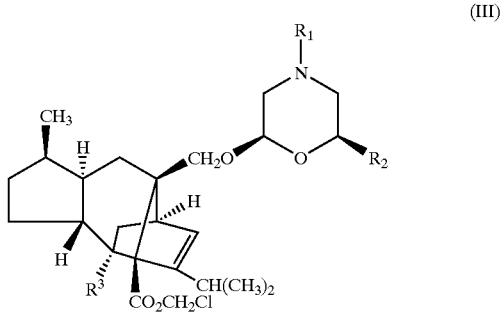

(III)

with the acid (IV; $HOCO(O)pR_5$ wherein $R_5$ has the meaning given in formula (I) or is a protected derivative thereof) or an alkali metal salt thereof in a solvent such as an aprotic solvent e.g. an aromatic hydrocarbon e.g. toluene or an ether e.g. tetrahydrofuran or mixtures thereof, followed by removal of any protecting groups.

The chloromethyl ester (III) may be prepared by treating the corresponding carboxylic acid of formula (II), with the chloromethyl derivative (V; $ClCH2SO_3$ Cl) in the presence of a base such as sodium bicarbonate and in a solvent such as a halohydrocarbon e.g. dichloromethane or an aqueous mixture thereof.

Acid addition salts of compounds of formula (I) may be prepared by treating a solution of compound of formula (I) in a suitable solvent e.g. an ether such as diethyl ether or diisopropyl ether or an alkanol e.g. ethanol with an aqueous solution of the appropriate acid e.g. hydrochloric acid. The desired salt may then be isolated using conventional procedures.

The following examples, which are non-limiting illustrate the invention.

The intermediates and examples have been characterised by NMR determined on a Varian Unity 300 $MH_z$ apparatus.

Intermediates 1 and 2 were prepared as described in WO99/58512.

INTERMEDIATE 1

[1R-(1α,3aβ,4β,4aβ,7β,7aα,8aβ)]8a-[(2R,6R)-(4-Allyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic Acid

INTERMEDIATE 2

[1R-(1α,3aβ,4β,4aβ,7β,7aα,8aβ)]8a-[(2R,6R)-(4-(2-Chloroallyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic Acid

EXAMPLE 1

General Procedure

Sodium hydrogen carbonate (5 eq) and tetrabutylammonium iodide (1.01 eq) were added to a stirred suspension of Intermediate 1 or 2 (1 eq) in ethyl acetate (7 ml/mmol). The mixture was maintained at room temperature for 30 minutes and the alkyl chloride or bromide ($Y—CH(R_4)OCO(O)pR_5$) (1.3 eq) was then added before the temperature was raised to 70° C. and maintained for two hours. The crude was diluted with more ethyl acetate (100 ml) and washed successively with aq. sodium metabisulfite, aq. sodium hydrogen carbonate and brine. The organic layer was dried over anhydrous sodium sulfate and concentrated. The residue was purified by column chromatography and the compound was obtained as its salt after the addition of the corresponding acid to a solution of the free azaderivative in an organic solvent.

EXAMPLE 1A

[[1R-(1α,3aβ,4β,4aβ,7β,7aα,8aβ)]8a-[(2R,6R)-(4-allyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid, pivaloyloxymethyl ester (1.5 g) was obtained as an amorphous residue following the procedure described above from Intermediate 1 (1.28 g) with pivaloyloxymethyl chloride (0.5 ml) and after a chromatographic purification using 1.5% methanol in dichloromethane as eluent.

$^1$H-NMR ($CDCl_3$,ppm): 9.70 (s, 1H, CHO), 6.07 (dd, 1H, H-2, J=1.5 and 3.6 Hz), 5.90 and 5.78 (AB system, 2H, $CH_2(COO)_2$, J=5.7 Hz), 5.82 (m, 1H, HC=C), 5.18 (m, 2H, $H_2C$=C), 4.38 (dd, 1H, H-2', J=2.1 and 8.4 Hz), 3.89 and 3.66 (AB system, 2H, 8a-$CH_2$, J=9.3 Hz), 3.65 (m, 1H, H-6'), 2.98 (dm, 2H, $CH_2N$, J=6.6 Hz), 2.83 (dm, 1H, H-3'$_a$, J=10.5 Hz), 2.75 (t, 1H, H-1, J=4.2 Hz), 2.67 (dm, 1H, H-5'$_a$, J=11.1 Hz), 1.22 (s, 9H, $(CH_3)_3C$).

EXAMPLE 1B

[[1R-(1α,3aβ,4β,4aβ,7β,7aα,8aβ)]8a-[(2R,6R)-(4-allyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid, 1-ethoxycarbonyloxy-ethyl ester (0.53 g) was obtained as an amorphous residue of a 1:1 diastereoisomeric mixture following the procedure described above from Intermediate 1 (0.5 g) with 1-choroethyl ethyl carbonate (0.2 ml) and after a chromatographic purification using hexane:ethyl acetate 4:1 as eluent.

$^1$H-NMR ($CDCl_3$,ppm): 9.74 and 9.67 (2s, 1H, CHO), 6.91 and 6.86 (2q, 1H, $CHCH_3$, J=5.1 Hz), 6.07 and 6.05 (2dd, 1H, H-2, J=1.5 and 3.3 Hz), 5.81 (m, 1H, CH=C), 5.17 (m, 2H, $CH_2$=C), 4.39 (m, 1H, H-2'), 4.23 (m, 2H, $OCOOCH_2$), 3.97 and 3.92 (AB system, 1H, 8a-$CH_{2a}$, J=9.3 Hz), 3.66 (m, 2H, 8a-$CH_{2b}$ and H-6'), 2.98 (bd, 2H, $CH_2N$, J=6.6 Hz), 2.85 (bd, 1H, H-3'$_a$, J=10.8 Hz), 2.76 (t, 1H, H-1, J=3.9 Hz), 2.68 (bd, 1H, H-5'$_a$, J=11.1 Hz), 1.55 (d, 3H, C$\underline{H}_3$CH, J=5.4 Hz).

EXAMPLE 1C

[[1R-(1α,3aβ,4β,4aβ,7β,7aα,8aβ)]8a-[(2R,6R)-(4-allyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid, phthalidyl ester (0.39 g) was obtained as an amorphous residue of a 1:1 diastereoisomeric mixture following the procedure described above from Intermediate 1 (0.335 g) with isobenzofuranone bromide (0.18 g) and after a chromatographic purification using hexane:ethyl acetate 3:1 as eluent.

$^1$H-NMR ($DMSOd_6$,ppm): 9.51 and 9.48 (2s, 1H, CHO), 7.98–7.63 (m, 5H, Ar and C$\underline{H}$OOC), 6.13 (dd, 1H, H-2, J=1.5 and 3.6 Hz), 5.75 (m, 1H, CH=C), 5.13 (m, 2H, CH$_2$=C), 4.24 and 4.21 (2m, 1H, H-2'), 3.61–3.38 (m, 3H, 8a-CH$_2$ and H-6'), 2.89 (bd, 2H, CH$_2$N, J=10.5 Hz), 2.70–2.56 (m, 3H, H-3'$_a$, H-5'$_a$ and H-1).

EXAMPLE 1D

[[1R-(1α,3aβ,4β,4aβ,7β,7aα,8aβ)]8a-[(2R,6R)-(4-(2-chloroallyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid, phthalidyl ester (0.31 g) was obtained as an amorphous residue of a 1:1 diastereoisomeric mixture following the procedure described above from Intermediate 2 (0.31 g) with isobenzofuranone bromide (0.18 g) and after a chromatographic purification using 12% acetone in hexane as eluent.

$^1$H-NMR (CDCl$_3$,ppm): 9.70 and 9.57 (2s, 1H, CHO), 7.98–7.52 (m, 4H, Ar), 7.51 and 7.46 (2s, 1H, CH(OOC)), 6.09 (m, 1H, H-2), 5.37–5.34 (m, 2H, H$_2$C=C), 4.37 (m, 1H, H-2'), 3.83 and 3.65, 3.78 and 3.62 (2 AB systems, 2H, 8a-CH$_2$, J=9.3 Hz), 3.66 (m, 1H, H-6'), 3.11 (s, 2H, CH$_2$N), 2.77 (m, 2H, H-3'$_a$ and H-1), 2.66 (m, 1H, H-5'$_a$), 2.28 (m, 1H, CH(CH$_3$)$_2$).

EXAMPLE 2

[[1R-(1α,3aβ,4β,4aβ,7β,7aα,8aβ)]8a-[(2R,6R)-(4-allyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid, 1-ethoxycarbonyloxy-ethyl ester hydrochloride (0.48 g) was isolated as a diastereoisomeric mixture of the salt prepared from a solution of Example 1b (0.59 g) in ethanol (10 ml) treated with 1N hydrochloric acid (1 ml) and concentrated.

$^1$H-NMR (CDCl$_3$,ppm): 13.43 (bs, 1H, N$^+$H), 9.70 and 9.62 (2s, 1H, CHO), 6.93 and 6.86 (2q, 1H, CHCH$_3$, J=5.4 Hz), 6.17 (m, 1H, HC=C), 6.09 (m, 1H, H-2), 5.56 (m, 2H, CH$_2$=C), 5.01 (m, 1H, H-2'), 4.34 (m, 1H, H-6'), 4.23 (m, 2H, CH$_2$CH$_3$), 4.02 and 3.75, 3.97 and 3.72 (2 AB systems, 2H, 8a-CH$_2$, J=8.7 Hz), 3.56 (m, 2H, CH$_2$N), 3.35 (bd, 1H, H-3'$_a$, J=11.4 Hz), 3.25 (bd, 1H, H-5'$_a$, J=12 Hz), 2.69 (t, 1H, H-1, J=3.9 Hz), 1.55 (d, 3H, CH$_3$CH, J=5.4 Hz).

EXAMPLE 3

[[1R-(1α,3aβ,4β,4aβ,7β,7aα,8aβ)]8a-[(2R,6R)-(4-allyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid, 1-ethoxycarbonyloxy-ethyl ester hydrochloride (0.13 g) was isolated as a diastereoisomeric pure compound after selective precipitation of the salt formed from Example 1b (0.28 g) in solution of diethyl ether treated with concentrated hydrochloric acid (0.04 ml).

$^1$H-NMR (CDCl$_3$,ppm): 13.4 (bs, 1H, N$^+$H), 9.62 (s, 1H, CHO), 6.86 (q, 1H, CHCH$_3$, J=5.4 Hz), 6.23–6.10 (m, 1H, CH=C), 6.08 (dd, 1H, H-2, J=1.5 and 3.6 Hz), 5.61–5.49 (m, 2H, CH$_2$=C), 5.01 (bd, 1H, H-2', J=7.5 Hz), 4.32 (m, 1H, H-6'), 4.23 (m, 2H, OCH$_2$CH$_3$), 4.02 and 3.72 (AB system, 2H, 8a-CH$_2$, J=9.0 Hz), 3.55 (m, 2H, CH$_2$N), 3.35 (bd, 1H, H-3'$_a$, J=11.7 Hz), 3.25 (bd, 1H, H-5'$_a$, J=12 Hz), 2.69 (t, 1H, H-1, J=3.9 Hz), 1.55 (d, 3H, CHCH$_3$, J=5.4 Hz).

EXAMPLE 4

[[1R-(1α,3aβ,4β,4aβ,7β,7aα,8aβ)]8a-[(2R,6R)-(4-allyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid, phthalidyl ester hydrochloride (0.3 g) was isolated as a diastereoisomeric mixture of the salt prepared from a solution of Example 1 c (0.29 g) in diethyl ether (10 ml) treated with concentrated hydrochloric acid (0.04 ml) and concentrated.

$^1$H-NMR (CDCl$_3$,ppm): 13.30 (bs, 1H, N$^+$H), 9.61 and 9.60 (2s, 1H, CHO), 7.97–7.47 (m, 5H, Ar and CH(OOC)), 6.20–6.05 (m, 2H, CH=C and H-2), 5.58–5.47 (m, 2H, CH$_2$=C), 4.93 (m, 1H, H-2'), 4.20 (m, 1H, H-6'), 3.91 and 3.71, 3.81 and 3.66 (2 AB systems, 2H, 8a-CH$_2$, J=9.0 Hz), 3.53 (m, 2H, CH$_2$N), 3.30 (bd, 1H, H-3'$_a$, J=11.4 Hz), 3.22 (m, 1H, H-5'$_a$), 2.70 (t, 1H, H-1, J=3.6 Hz).

EXAMPLE 5

[[1R-(1α,3aβ,4β,4aβ,7β,7aα,8aβ)]8a-[(2R,6R)-(4-allyl-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid, pivaloyloxymethyl ester hydrochloride (0.98 g) was prepared by addition of concentrated hydrochloric acid (0.15 ml) to a solution of Example 1a (1.1 g) in diisopropyl ether (25 ml) at 0° C., and isolated after washing and triturating the precipitate thus formed.

$^1$H-NMR (CDCl$_3$,ppm): 13.4 (bs, 1H N$^+$H), 9.67 (s, 1H, CHO), 6.17 (m, 1H, CH=C), 6.09 (dd, 1H, H-2, J=1.2 and 3.3 Hz), 5.84 (AB system, 2H, CH$_2$(COO)$_2$, J=5.4 Hz), 5.56 (m, 2H, CH$_2$=C), 5.02 (bd, 1H, H-2', J=7.8 Hz), 4.34 (m, 1H, H-6'), 3.95 and 3.73 (AB system, 2H, 8a-CH$_2$, J=9.0 Hz), 3.56 (m, 2H, CH$_2$N), 3.36 (bd, 1H, H-3'$_a$, J=12 Hz), 3.25 (bd, 1H, H-5'$_a$, J=11.4 Hz), 2.28 (t, 1H, H-1, J=3.9 Hz), 1.22 (s, 1H, 9H, (CH$_3$)$_3$C).

EXAMPLE 6

[[1R-(1α,3aβ,4β,4aβ,7β,7aα,8aβ)]8a-[(2R,6R)-(4-(2-chloroallyl)-6-methyl-morpholin-2-yl)-oxymethyl]-4-formyl-4,4a,5,6,7,7a,8,8a-octahydro-7-methyl-3-(1-methylethyl)-1,4-methano-s-indacene-3a(1H)-carboxylic acid phtalidyl ester hydrochloride (0.3 g) was isolated as a diastereoisomeric mixture of the salt prepared from a solution of Example 1d (0.3 g) in diethyl ether (3 ml) treated with concentrated hydrochloric acid (0.04 ml) and concentrated.

$^1$H-NMR (CDCl$_3$,ppm): 13.8 (bs, 1H, N$^+$H), 9.61 and 9.60 (2s, 1H, CHO), 8.00–7.47 (m, 5H, Ar and CH(OOC)), 6.11 (dd, 1H, H-2, J=1.5 and 3.6 Hz), 6.90 (m, 2H, CH$_2$=C), 5.00 (m, 1H, H-2'), 4.20 (m, 1H, H-6'), 3.92 and 3.73 (AB system, 1H, 8a-CH$_2$, 1$^{st}$ isomer, J=9.0 Hz), 3.82 and 3.67 (m and AB system, 3H, CH$_2$N and 8a-CH$_2$, 2$^{nd}$ isomer, J=9.0 Hz), 3.3 and 3.2 (2m, 2H, H-3'$_a$ and H-5'$_a$), 2.71 (t, 1H, H-1, J=3.9 Hz).

Pharmacy Examples

| 1. Conventional oral tablet | |
| --- | --- |
| Drug substance | 100 mg |
| Microcrystalline cellulose | 160 mg |
| Crosscarmellose sodium | 20 mg |
| Magnesium stearate | 5 mg |

The drug substance is blended with microcrystalline cellulose, crosscannellose sodium and magnesium stearate, then compressed into tablets.

| 2. Conventional Capsule | |
|---|---|
| Drug substance | 100 mg |
| Lactose | 200 mg |
| Magnesium stearate | 2 mg |

The drug substance is blended with the lactose and the magnesium stearate and then filled into appropriate capsules.

Antifungal Activity

Compounds of formula (I) have been tested for antifungal activity in a standard in vitro screen and the minimum inhibiting concentration (MIC;μg/ml) determined for each compound against a relevant strain of Candida albicans in the presence or absence of mouse serum. The results obtained with representative compounds of the invention are given below.

| Compound | Example 5 | Example 3 | Example 2 | Example 4 |
|---|---|---|---|---|
| C.albicans4711 | >125 | 62 | 8 | NT |
| 50%serum C.albicans4711 | 0.05 | 0.06 | 0.12 | 0.25 |

What is claimed is:

1. A compound of formula (I)

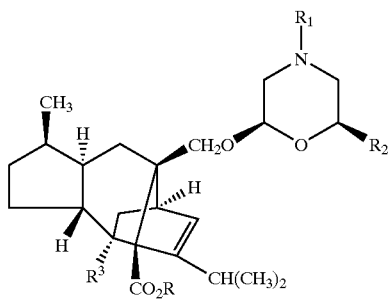

(I)

and physiologically acceptable salts
wherein:

$R^1$ is selected from the group consisting of
  $C_{1-6}$ straight or branched chain alkyl,
  $C_{1-6}$ straight or branched chain alkoxy, optionally substituted phenoxy,
  $C_{3-6}$ straight or branched chain, alkenyloxy, optionally substituted by 1 or 2 halogen atoms, and
  $C_{1-4}$ straight or branched alkoxy substituted by an optionally substituted phenyl group,
  $C_{3-8}$ straight or branched chain alkynyl,
  $C_{3-6}$ straight or branched chain alkenyl, optionally substituted by $C_{1-4}$ alkoxy or 1 or 2 halogen atoms,
  optionally substituted phenyl,
  optionally substituted $C_{3-7}$ cycloalkyl,
  optionally substituted $C_{5-7}$ cycloalkenyl,
  $C_{2-4}$ straight or branched chain alkyl substituted by a group selected from the group consisting of $C_{1-4}$ alkoxy, $C_{1-4}$ alkyl thio and halogen,
  $C_{1-4}$ straight or branched chain alkyl substituted by a group selected from the group consisting of $C_{1-4}$ alkoxycarbonyl, arylalkyloxycarbonyl, aryloxycarbonyl, propadienyl, cyano, optionally substituted $C_{3-7}$ cycloalkyl, optionally substituted 5 or 6 membered heteroaryl, and 1 or 2 optionally substituted phenyl groups,
  and methyl substituted by $C_{1-6}$ alkanoyl, optionally substituted benzoyl;

$R_2$ is a group selected from hydrogen, $C_{1-6}$ straight or branched chain alkyl, $C_{3-6}$ straight or branched chain alkenyl, optionally substituted phenyl and $C_{1-4}$ alkyl substituted with a group selected from $C_{1-4}$ alkoxy hydroxy, acyloxy, alkoxycarbonyl and aryloxycarbonyl;

$R_3$ is a group selected from formyl or cyano;

R is phthalidyl, (2-oxo-5-methyl-1,3-dioxoblen-4-yl) methyl or the group $CHR_4OCO(O)pR_5$ wherein $R_4$ is hydrogen or $C_{1-4}$ alkyl, p is zero or 1 and wherein $R_5$ is $C_{1-6}$ alkyl, $C_{5-8}$ cycloalkyl, optionally substituted by $C_{1-3}$ alkyl or carboxyl, $C_{1-4}$ alkyl substituted by $C_{1-3}$ alkoxy or carboxyl, $C_{1-6}$ alkyl substituted by one or more groups selected from amino, $C_{1-4}$ alkylamino di($C_{1-4}$ alkyl)amino or carboxyl, phenyl, optionally substituted by carboxyl or aminoalkyl, a $C_{1-4}$ alkylaminoalkyl or
di($C_{1-4}$ alkyl)aminoalkyl, or $R_5$ is a 5–8 membered heterocyclic group containing 1 or 2 heteroatoms selected from oxygen or nitrogen.

2. A compound as claimed in claim 1 wherein $R_3$ is formyl.

3. A compound is as claimed in claim 1 wherein $R_2$ is methyl.

4. A compound as claimed in claim 1 wherein R is a group selected from phthalidyl and $CH(R_4)OCO(O)_pR_5$ wherein $R_4$ is hydrogen or methyl and $R_5$ is ethyl or t-butyl.

5. A compound as claimed in claim 1 wherein $R_1$ is a group selected from methyl, ethyl, propyl, isopropyl, butyl, 1-methylpropyl, 3-methylbutyl, allyloxy, 2-chloroallyloxy, methoxy, cyclopropyl, allyl, 2-chloroallyl, 2-bromoallyl, 2-methylallyl, 3-3-difluoroallyl, 2,3-butadienyl, phenyl, ethylthioethyl, methoxyethyl, benzyl, furylmethyl, 2,6-difluorophenylmethyl, 3,4-difluorophenylmethyl, 3,5-difluorophenylmethyl, 3,5-difluorophenylmethyl, 3,4-methylenedioxyphenylmethyl, 4-methoxyphenylmethyl, 1-phenylethyl and 2-propynyl.

6. A pharmaceutical composition comprising a compound as claimed in claim 1 in admixture with one or more physiologically acceptable carriers or excipients.

7. A method for the prevention or treatment of a fungal or protozoal infection in an animal, which method comprises administering to said animal an effective amount of a compound as claimed in claim 1.

8. A method of treatment as claimed in claim 7 wherein the animal is a human.

9. A process for the preparation of a compound of claim 1, which comprises:

esterification of the corresponding carboxylic acid (II) or an alkali metal salt thereof wherein $R_1$, $R_2$ and $R_3$ have the meaning defined in formula (I),

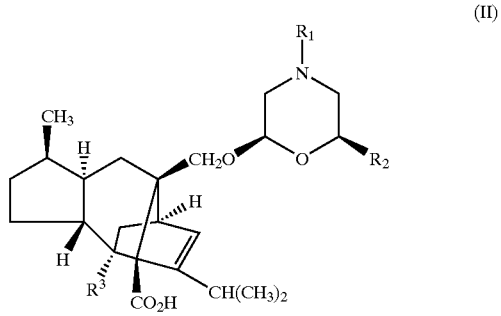

(II)

by reaction with the compound RY wherein R has the meanings defined in formula (I) or is a group convertible thereto and Y is a leaving group.

10. A process for preparing a compound of claim 1 wherein R is the group CHR$_4$OCO(O)pR$_5$ and R$_4$ is hydrogen by reacting the halomethyl ester (III), wherein R$_1$, R$_2$ have the meaning given in formula I, and R$_3$ is formyl or a protected formyl group,

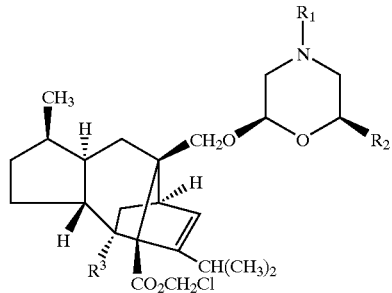

with an acid having the formula, HOCO(O)pR$_5$, wherein R$_5$ has the meaning given in formula (I) or is a protected derivative thereof or is an alkali metal salt thereof; and if necessary or desired followed by removal of any protecting groups.

11. A compound as claimed in claim 1 wherein:

R$_1$ is a group selected from methyl, ethyl, propyl, isopropyl, butyl, 1-methylpropyl, 3-methylbutyl, allyloxy, 2-chloroallyloxy, methoxy, cyclopropyl, allyl, 2-chloroallyl, 2-bromoallyl, 2-methylallyl, 3-3-3-difluoroallyl, 2,3-butadienyl, phenyl, ethylthioethyl, methoxyethyl, benzyl, furylmethyl, 2,6-difluorophenylmethyl, 3,4-difluorophenylmethyl, 3,5-difluorophenylmethyl, 3,5-difluorophenylmethyl, 3,4-methylenedioxyphenylmethyl, 4-methoxyphenylmethyl, 1-phenylethyl and 2-propynyl;

R$_2$ is methyl;

R$_3$ is formyl; and

R is a group selected from phthalidyl and CH(R$_4$)OCO(O)$_p$R$_5$, wherein R$_4$ hydrogen or methyl and R$_5$ is ethyl or t-butyl.

* * * * *